(12) United States Patent  
Lichtman et al.

(10) Patent No.: US 6,869,772 B2  
(45) Date of Patent: Mar. 22, 2005

(54) METHOD FOR LABELING INDIVIDUAL CELLS

(75) Inventors: Jeff W. Lichtman, St. Louis, MO (US); Wai T. Wong, Philadelphia, PA (US); Rachel Wong, University City, MO (US); Wen-Biao Gan, New York, NY (US); Jamie Grutzendler, St. Louis, MO (US)

(73) Assignee: Washington University, Saint Louis, MO (US)

( * ) Notice: Subject to any disclaimer, the term of this patent is extended or adjusted under 35 U.S.C. 154(b) by 99 days.

(21) Appl. No.: 09/802,644

(22) Filed: Mar. 9, 2001

(65) Prior Publication Data

US 2002/0155520 A1 Oct. 24, 2002

Related U.S. Application Data

(60) Provisional application No. 60/188,370, filed on Mar. 10, 2000.

(51) Int. Cl.$^7$ .......................... G01N 1/30; C12N 15/87
(52) U.S. Cl. ...................... 435/40.5; 435/459; 427/2.13
(58) Field of Search ............................... 435/40.5, 459; 427/2.13

(56) References Cited

U.S. PATENT DOCUMENTS

| | | | |
|---|---|---|---|
| 4,326,524 A | | 4/1982 | Drake, Jr. et al. |
| 4,945,050 A | | 7/1990 | Sanford et al. |
| 5,036,006 A | | 7/1991 | Sanford et al. |
| 5,100,792 A | | 3/1992 | Sanford et al. |
| 5,179,022 A | | 1/1993 | Sanford et al. |
| 5,204,253 A | | 4/1993 | Sanford et al. |
| 5,371,015 A | | 12/1994 | Sanford et al. |
| 5,436,134 A | * | 7/1995 | Haugland et al. ............. 435/29 |
| 5,466,587 A | * | 11/1995 | Fitzpatrick-McElligott et al. ......................... 424/489 |
| 5,478,744 A | | 12/1995 | Sanford et al. |
| 5,573,909 A | | 11/1996 | Singer et al. |
| 5,656,449 A | * | 8/1997 | Yue ............................. 435/26 |
| 5,723,218 A | | 3/1998 | Haugland et al. |
| 5,849,526 A | * | 12/1998 | Pichersky ................... 435/243 |
| 5,888,829 A | * | 3/1999 | Gee et al. .................... 210/649 |
| 6,013,486 A | * | 1/2000 | Dellaporta ..................... 435/6 |
| 6,290,991 B1 | * | 9/2001 | Roser et al. ................ 424/500 |

FOREIGN PATENT DOCUMENTS

WO      WO 0169244 A2 * 9/2001 .......... G01N/33/50

OTHER PUBLICATIONS

Wissing et al. "Illumination of the Malaria Parasite Plasmodium falciparum Alters Intracellular pH" (2002) J. Biol. Chem., 277 (40), 37747–37755.*

Davey et al., "Flow Cytometry of Microorganisms–Chapter 4" (1993) pp. 1–9 and pp. 1–18 of bibliography, accessed on the Internet at: pcfcij.dbs.ac.uk/thesis/tchap4.html on Feb. 27, 2003.*

"Sigma–Aldrich Catalog—Fluorescent Probes" pp. 1–4, accessed on the Internet at: www.sigmaaldrich.com/Brands/Fluka_Riedel_Home/Analytical/Fluorescent_Probes/Product_vs_Methodology/Miscellaneous.html on Feb. 27, 2003.*

Gan Wen–Biao et al., "Multicolor "Diolistic" labeling of the nervous system using lipophilic dye combinations" Neuron. Aug. 2000. pp. 219–225. vol. 27, No. 2. ISSN: 0896–6273.

Wong W T et al., "Multicolor diolistic labeling of the nervous system using lipophilic dye combinations." Society for Neuroscience Abstracts. Pgs. Abstract No. 125.10. vol. 26, No. 1–2, 2000. 30th Annual Meeting of the Society of Neuroscience; New Orleans, LA, USA; Nov. 04–09, 2000: ISSN: 0190–5295.

Kettunen P et al., "Rapid loading of calcium indicators by particle mediated ballistic delivery." Society for Neuroscience Abstracts. p. 1008. vol. 27, No. 1. 2001; 31st Annual Meeting of the Society for Neuroscience; San Diego, California, USA, Nov. 10–15, 2001. ISSN: 0190–5295.

Betz et al., "Activity–dependent Fluorescent Staining and Destaining of Living Vertebrate Motor Nerve Terminals", *J. Neurosci.*, 1992, 12:363–75.

Chalfie et al., "Green Fluorescent Protein as a Marker for Gene Expression",*Science*, 1994, 263:802–805.

Craig et al., "The Distribution of Glutamate Receptors in Cultured Rat Hippocampal Neurons: Postsynaptic Clustering of AMPA–Selective Subunits" *Neuron*, 1993, 10:1055–1068.

Dunaevsky et al., "Developmental regulation of spine motility in the mammalian central nervous system", *Proc. natl. Acad. Sci. USA*, 1999, 96:13438–13443.

Gan and Macagno, "Developing Neurons Use a Putative Pioneer's Peripheral Arbor to Establish Their Terminal Fields", *J. Neurosci.*, 1995, 5:3254–3262.

Gan and Lichtman, "Synaptic Segregation at the Developing Neuromuscular Junction", *Science*, 1998, 282:1508–1511.

Gan et al., "Vital imaging and ultrastructural analysis of individual axon terminals labeled by iontophoretic application of lipophilic dye", *Neurosci. Methods*, 1999, 93:13–20.

* cited by examiner

*Primary Examiner*—Jon P. Weber  
(74) *Attorney, Agent, or Firm*—Senniger, Powers, Leavitt & Roedel

(57) ABSTRACT

A method is provided for the labeling of individual cells. Labeling is accomplished by coating a particle with at least one dye or nucleic acid sequence encoding a marker protein. The particle is then propelled toward the cell resulting in the particle contacting the cell for a time sufficient for the dye or nucleic acid to leave the particle and enter the cell. The present method allows for the differential labeling of individual cells within dense populations of cells.

54 Claims, 7 Drawing Sheets

FIG. 2A
FIG. 2B
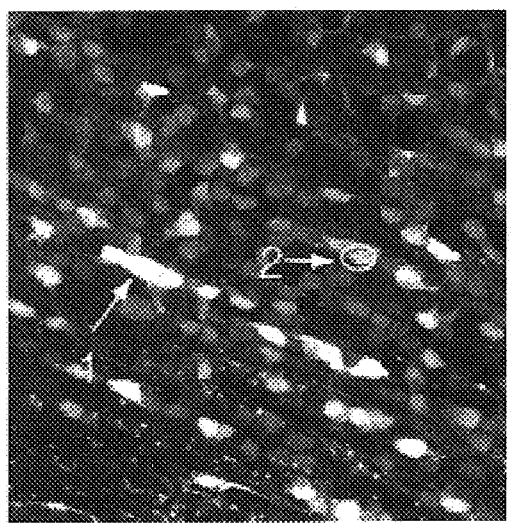
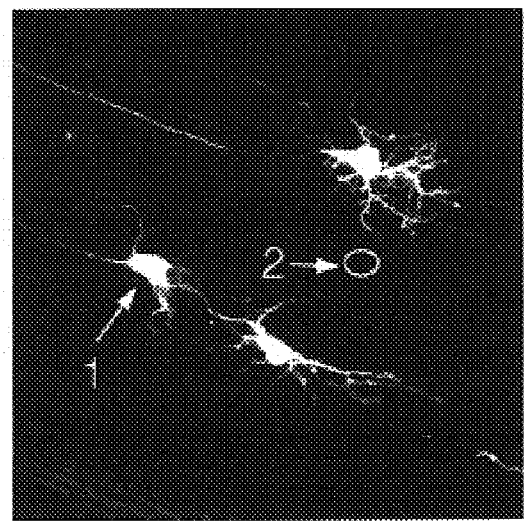

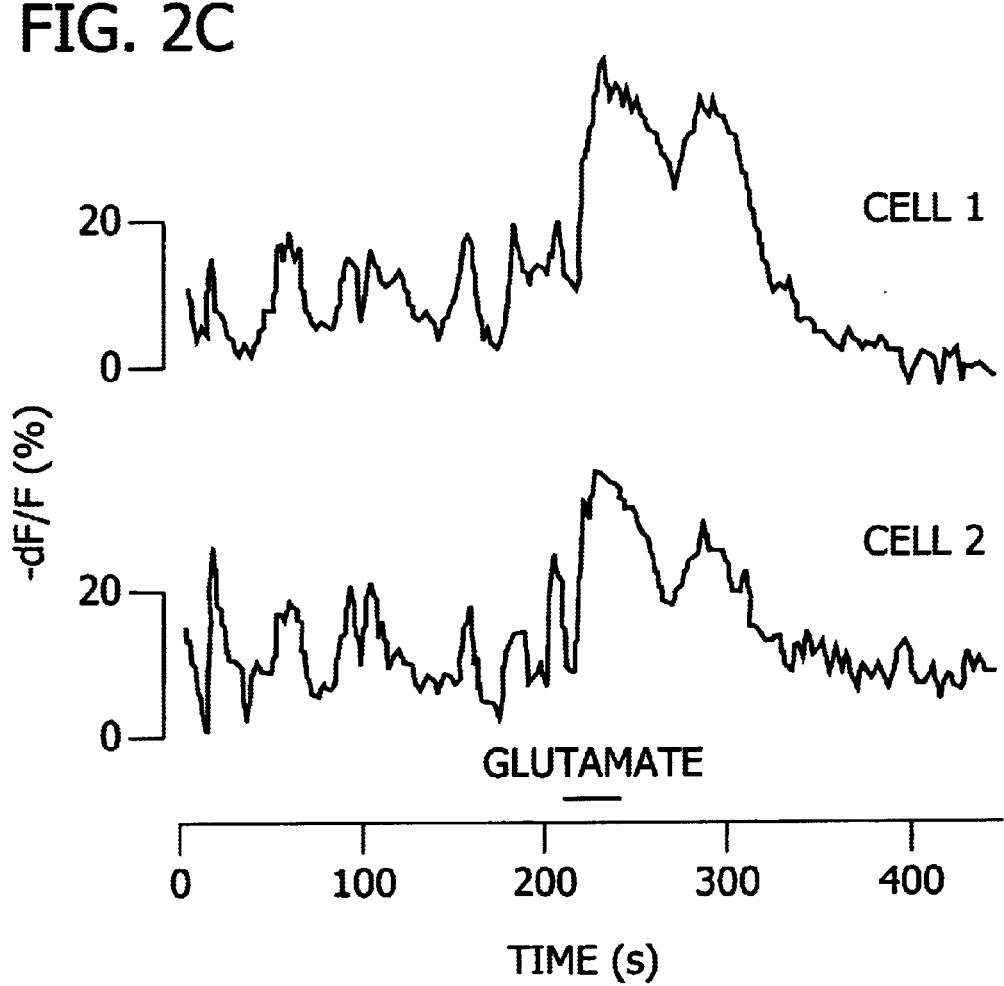

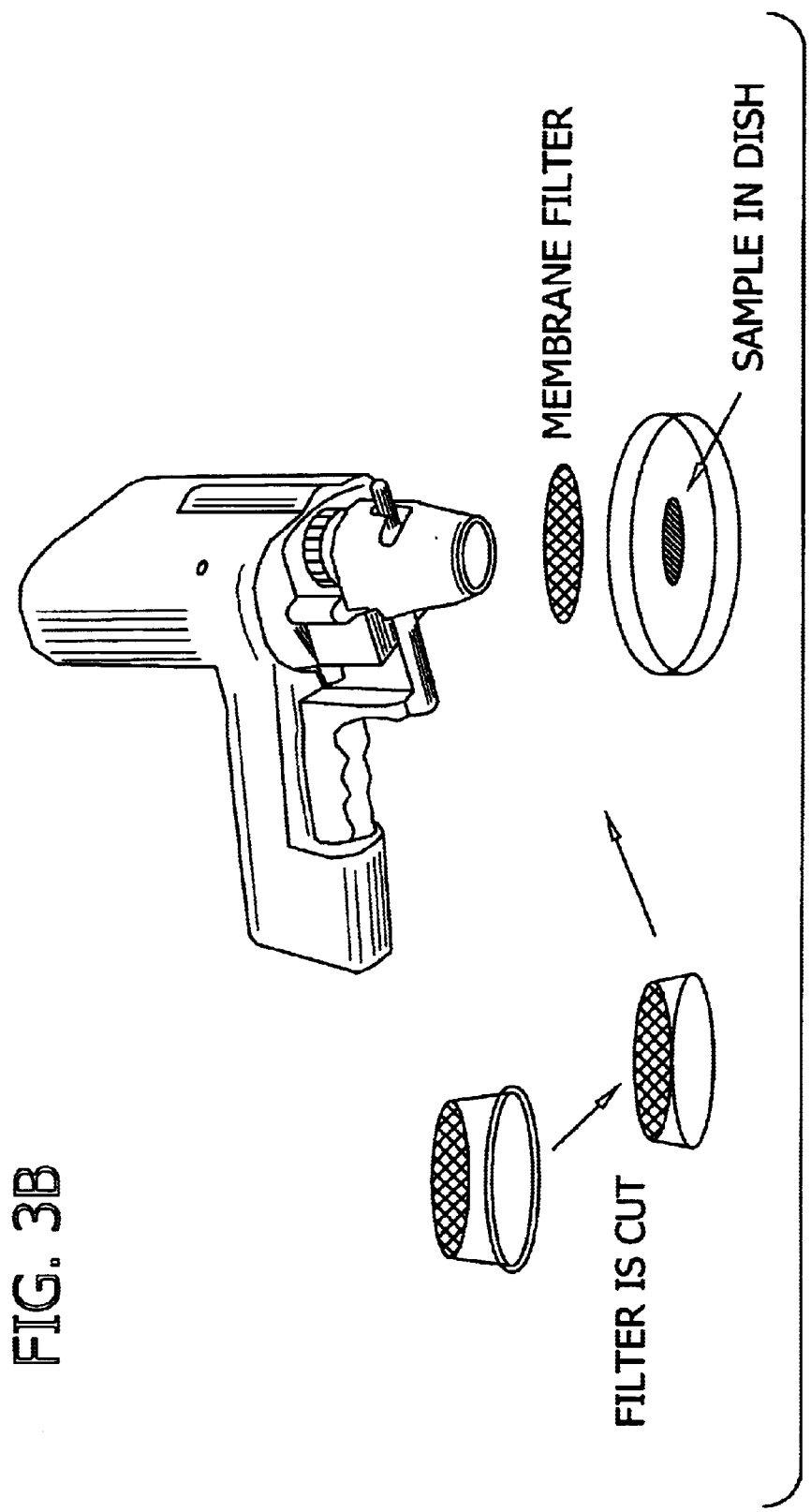

METHOD FOR LABELING INDIVIDUAL CELLS

CROSS-REFERENCE TO RELATED APPLICATIONS

This application claims the benefit of U.S. Provisional Patent Application Ser. No. 60/188,370, filed Mar. 10, 2000, which is herein incorporated by reference in its entirety for all purposes.

BACKGROUND

Beginning a century ago with the Golgi stain technique, neuronal labeling has played a central role in the study of anatomical and physiological systems. The Golgi stain technique utilizes silver impregnation of fixed tissues and allows imaging of the smallest objects that are resolvable using a light microscope. Using the Golgi technique, entire neurons, including the dendrites and axons, could be imaged for the first time. Subsequently, fluorescence techniques were developed in order to study living neural preparations. Fluorescent dyes that vitally label organelles concentrated in synapses (Magrassi et al., *J Neurosci.*, 1987, 7:1207–14) or that mark synapses due to vesicular recycling (Lichtman et al., 1985, *Nature* 314:357–9; Betz et al., *J. Neurosci.*, 1992, 12:363–75) have provided a means to study dynamic aspects of neuronal connections.

Recently, dipyrromethene boron difluoride labeled flourescent microparticles used for labeling were disclosed in Haugland et al., U.S. Pat. No. 5,723,218. Haugland et al. teach the use of derivatives of dipyrromethene boron difluoride dyes incorporated internally into polymeric microparticles having a diameter of between 0.01 micrometers and about 50 micrometers in order to produce a dye impregnated particle that can fluoresce for extended periods of time. Thus, in Haugland et al., the dye is not released from the particle, but the particles are themselves used as fluorescent indicators.

A method of labeling cells using a series of fluorescent dyes was also developed by Singer et al., U.S. Pat. No. 5,573,909. Singer et al. disclose methods for labeling target materials using a series of particles that internally incorporate two or more dyes having overlapping excitation and emission spectra. Both a donor and a transfer dye are used. According to Singer et al., the target materials are labeled by combining the particles with a sample containing the target material. The Singer technique requires the use of a two-step process in which the sample to be studied is first pre-labeled with a fluorescent marker such as an antibody. Subsequently, the particles are added to the sample such that the fluorescent antibody interacts with the particles to generate fluorescence resonance energy transfer (FRET), which is detected with a camera. The dye is not released from the particles in the Singer method. Therefore, the entire surface of a target cell is not labeled.

One approach which has been developed to label an entire cell is the introduction and expression of Green Fluorescent Protein (GFP). GFP and its variants have been used to label cells in transgenic animals (e.g., Chalfie et al., 1994, *Science*, 263:802–805; van den Pol and Ghosh, 1998, *J. Neurosci.*, 18:10640–10651). GFP is a spontaneously fluorescent protein isolated from coelenterates, such as the Pacific jellyfish, *Aequoria victoria*. GFP serves to transduce, by energy transfer, the blue chemiluminescence of another protein, aequirin, into green fluorescent light. GFP can also function as a protein tag, as it tolerates N— and C— terminal fusion to a broad variety of proteins, many of which have been shown to retain native function. When expressed in mammalian cells, fluorescence from wild type GFP is typically distributed throughout the cytoplasm and nucleus, but excluded from the nucleolus and vesicular organelles. The enormous flexibility of this material as a noninvasive marker in living cells allows for its use in numerous other applications such as a cell lineage tracer, reporter of gene expression, and as a potential measure of protein—protein interactions. Particle mediated gene transfer and viral transfection techniques (Lo et al., 1994, *Neuron* 13:1263–1268; Vasquez et al., 1998, *Exp. Neurol.*, 154:353–365.) have been successfully used to label cells with GFP. These newer techniques provide the kind of resolution obtained with the Golgi technique, but can be used in vivo.

Current vital labeling techniques have several limitations. First, it is difficult to label individual cells, such as neurons, differentially within complex biological networks. Although lipophilic carbocyanine dyes are available at many different excitation and emission profiles, they are typically applied to cells and tissues in ways that label many individual cells at the same wavelength (e.g., O'Rourke et al., 1994, *Neuron*, 12:921–934; Wu and Cline, 1998, *Science*, 279:222–226.). For example, according to one known technique, lipophilic crystals are placed on nerves or clusters of nerves causing tens or hundreds of neighboring cells to be labeled the same color (See Nakamura and O'Leary, 1989, *J. Neurosci.*, 9:3776–3795; Nakamoto et al. 1996, *Cell*, 86: 755–766). Pressure injection of carbocyanic dyes into cells is another technique that has been used (See, O'Rourke et al., 1994, *Neuron*, 12: 921–934 (labeling of axonal arbors); O'Rourke et al., 1997, *Development*, 124: 997–1005 (labeling of migrating cortical cells)). While both of these approaches use carbocyanine dyes, they both have the disadvantage of labeling large patches of cells with a single dye at the site of the application. Therefore, individual cells cannot be differentiated.

Individual cells have been labeled with carbocyanine dyes using iontophoretic injection (Wu and Cline, 1998, *Science*, 279:222–226). Lipophilic carbocyanine dyes have also been applied with sharp electrodes to label individual axons. (Gan and Macagno, 1995 *J. Neurosci.* 5:3254–3262; Gan and Lichtman, 1998, *Science*, 282:1508–1511, Gan et al., 1999, *J Neurosci. Methods*, 93:13–20.) However, these approaches are tedious, time consuming and only a small number of cells can be labeled at any one time. Attempts have been made to circumvent this limitation by sprinkling the dye crystals onto cells. However, this approach is highly variable because dye crystal size, density and penetration are difficult to control.

GFP expression utilizing gene guns and the use of gene guns for introducing materials into the interior of cells has been described in the following U.S. Patents: Drake, Jr. et al., U.S. Pat No. 4,326,524, Sanford U.S. Pat. No. 5,204,253, Sanford et al. U.S. Pat. No. 5,179,022, Sanford et al. U.S. Pat. No. 5,100,792, Sanford et al. U.S. Pat. No. 5,478,744, Sanford et al. U.S. Pat. No. 5,371,015, Sanford et al. U.S. Pat. No. 5,036,006 and Sanford et al. U.S. Pat. No. 4,945,050. When particles containing DNA encoding GFP enter a nucleus they can result in gene expression (Lo et al. 1994, *Neuron, 13:1263–1268*). GFP gene expression, however, usually takes more than 6 hours to occur after gene transfection in cell culture and brain slices. This waiting period limits many structural and functional studies, as frequently, considerable structural changes occur, e.g. in brain slices, during the first few hours after preparation (Kirov et al., 1999, *J. Neurosci.* 19:2876–86). In addition, the variety of distinct emission profiles available using this approach is limited. In GFP labeling, the emission profiles are directly related to the structure of the native protein which emits fluorescence. Currently, cells labeled using GFP labeling techniques may only be imaged at a relatively few non-overlapping excitation peaks. Further, the GFP transfection technique is very inefficient despite the use of high density particle delivery to the desired tissue with only a small fraction of cells penetrated by the particles expressing GFP. This limitation prevents the use of GFP transfection for the study of networks of neurons, because such studies require high density labeling such that the interactions between adjacent cells can be optically imaged.

A critical need exists, therefore, for a method of rapid, individualized labeling in cell culture or tissues that allows adjacent cells to be optically separated despite the use of high density labeling in both fixed and living tissues. As described below, Applicants have discovered such a method of rapid and individual labeling using microparticles that meets this need.

SUMMARY

The present method provides several advantages over previous labeling techniques. First, the labeling of individual cells is rapid and extensive, allowing, for example, the entire dendritic arbors of neurons to be labeled within minutes after dye-coated particles contact the cell. Such rapid labeling is especially useful in studying neuronal tissues such as brain slices due to their rapid deterioration after preparation. Second, the labeling technique involves passive dye transfer and diffusion that is independent of gene transcription and protein synthesis. Thus, all types of cells can be labeled in both fixed and living tissues. Third, using the present methods, individual axons can be labeled without the necessity of the particles reaching the cell body. According to the present method, the dye is released from the particle to diffuse along the cell's processes. Therefore, there is no need for the dye-coated particles to come into contact with the cell nucleus. Fourth, using various combinations of dyes, different neurons can be labeled at various non-overlapping excitation and emission profiles. Combined with high density labeling, this feature is potentially very useful in studying neuronal connections in complicated biological networks. Thus, the present techniques provide distinct advantages for medical diagnosis and research purposes.

Accordingly, in one aspect a method for labeling of individual cells is provided comprising providing at least one target cell; providing at least one particle coated with at least one dye; and propelling the coated particle toward the target cell to thereby cause the coated particle to contact the cell for a time sufficient to cause labeling of the target cell by release of the dye from the particle; and detecting the presence of the dye.

A further aspect provides a method for labeling of individual cells comprising providing at least one target cell having a cell membrane; providing at least one coated particle coated with at least one lipophilic dye and propelling the coated particle toward the target cell to cause said coated particle to contact the cell membrane for a time sufficient to cause labeling of the target cell by release of the dye from the particle; and detecting the presence of the dye.

Another aspect provides a method for labeling individual cells comprising providing a plurality of target cells; providing a plurality of particles coated with a plurality of dyes; and propelling the coated particles toward the target cells to thereby cause the coated particles to contact the cells for a time sufficient to cause labeling of the target cells by release of the dye from the particle; and detecting the presence of the dye.

In yet a another aspect, the present method can further comprise forming a macroprojectile containing a plurality of coated particles and still further comprise causing the macroprojectile to contact a macroprojectile stopping means before contacting the target cell.

In a further aspect, a method is provided for labeling individual cells comprising providing at least one particle containing at least one lipophilic dye selected from a group consisting of DiO, DiI, DiD and any combination thereof to form a coated particle; providing at least one target cell, the target cell having a cell membrane; propelling the coated particle toward the target cell to thereby cause the coated particle to contact the cell membrane for a time sufficient to cause labeling of the target cell by release of the dye from the particle; and detecting the presence of the dye.

Yet another aspect provides a method for labeling of individual cells comprising providing at least one particle containing at least one lipophilic dye that is a voltage sensitive dye and providing at least one target cell, the cell having a cell membrane. A coated particle is propelled toward the target cell to cause the coated particle to contact the cell membrane for a time sufficient to label the target cell by release of the dye from the particle. The presence of the dye is then detected by any suitable means.

A method for monitoring a physiological process in a cell is also provided. This method comprises providing at least one particle containing at least one dye that is sensitive to a physiological process; providing at least one living target cell; propelling the coated particle toward the target cell to cause the coated particle to contact the cell for a time sufficient to cause labeling of the target cell by release of the dye from the particle; detecting changes in the dye; and correlating the changes in the dye with changes in the physiological process within the target cell.

A method for determining changes in cell membrane voltage potential is further presented comprising providing at least one particle containing at least one dye that is a voltage sensitive dye; providing at least one target cell having a cell membrane, the cell membrane having an inner surface and an outer surface; propelling the coated particle toward the target cell to cause the coated particle to contact the cell for a time sufficient to cause labeling of the target cell by release of the dye from the particle; detecting changes in the dye; and correlating the dye changes with changes in cell membrane voltage potential.

An additional aspect provides a method for measuring membrane fluidity comprising providing at least one target cell, the target cell having a cell membrane; providing at least one coated particle that is coated with a least one lipophilic dye; propelling said coated particle toward said target cell to thereby cause the coated particle to contact the cell membrane for a time sufficient to cause labeling of the target cell by release of the dye from the particle; and detecting the movement of the dye in the membrane as a function of time.

The present method is also directed to a method for diagnosing a human, animal or plant disease, disorder or condition comprising providing at least one particle coated with at least one dye; providing at least one target cell; propelling the coated particle toward the target cell to cause said coated particle to contact the target cell for a time sufficient to cause labeling of the target cell by release of the dye from the particle; detecting of the presence of the dye; and utilization of the presence of the dye to diagnose the disease, disorder or condition.

Also provided is a method for studying the morphology of a cell comprising providing at least one particle coated with at least one dye; providing at least one target cell; propelling the coated particle toward the target cell to cause the coated particle to contact the target cell for a time sufficient to cause labeling of the target cell by release of the dye from the particle; and detecting the presence of the dye.

In yet another aspect provides a dye labeled tissue produced by a method comprising providing a target tissue, the target tissue comprising a plurality of target cells; providing a plurality of particles coated with at least one dye; and propelling the coated particles toward the target cells to cause the coated particles to contact the target cell for a time sufficient to cause the labeling of at least one target cell by release of the dye from the particle.

A method for labeling individual cells is further provided comprising, providing a plurality of target cells; providing a plurality of particles containing a plurality of nucleotide sequences encoding fluorescent proteins, each of the proteins having different emission spectrum; and propelling the plurality of particles toward the plurality of cells to cause the particles to enter the cells and reside in the interiors of the cells.

Also provided is a tissue comprising cells that are individually labeled with a plurality of dyes, wherein the majority of adjacent cells contain dyes with different emission spectra.

In yet another aspect, a dye labeled tissue is produced by a method comprising providing a target tissue, the target tissue comprising a plurality of target cells; providing a plurality of particles coated with at least one dye; and propelling the coated particles toward the target cells to thereby cause the coated particles to contact the target cell for a time sufficient to cause labeling of at least one target cell by release of the dye from the particle.

Other objects and features will be in part apparent and in part pointed out hereinafter.

DESCRIPTION OF THE DRAWINGS

These and other features, aspects, and advantages of the present method will become better understood with regard to the following description, appended claims and accompanying figures where:

FIG. 2A is a photograph of neurons in the ganglion cell layer in an intact piece of living retina imaged using two-photon microscopy. The neurons have been labeled with a calcium-sensitive fluorescent dye, Fura-2AM (775 nm. excitation, 522 nm. emission), that reports the physiological activity of neurons in terms of changes in their intracellular calcium concentrations.

FIG. 2B is an image of the same field of neurons in FIG. 2A, using filters that reveal the presence of 3 neurons that have been labeled by particle mediated delivery of DiI.

FIG. 2C is a graph showing the responses in Fura-2AM fluorescence in cells 1 (DiI labeled using the present method) and 2 (a nearby unlabeled cell) to the application of glutamate (100 $\mu$M) as assessed by calcium imaging. Labeled cells show normal physiological responses to the application of glutamate that are similar to those seen in unlabeled cells in the same field. This result indicates that the physiological responsiveness of neurons has not been compromised by the labeling procedure.

FIG. 2D illustrates that labeling using the present method does not exert deleterious effects that inhibit the process of dynamic remodeling in developing neurons.

FIG. 3B is an illustration of the use of a filter when propelling is accomplished by the use of a gene gun.

DEFINITIONS

Figure 1:
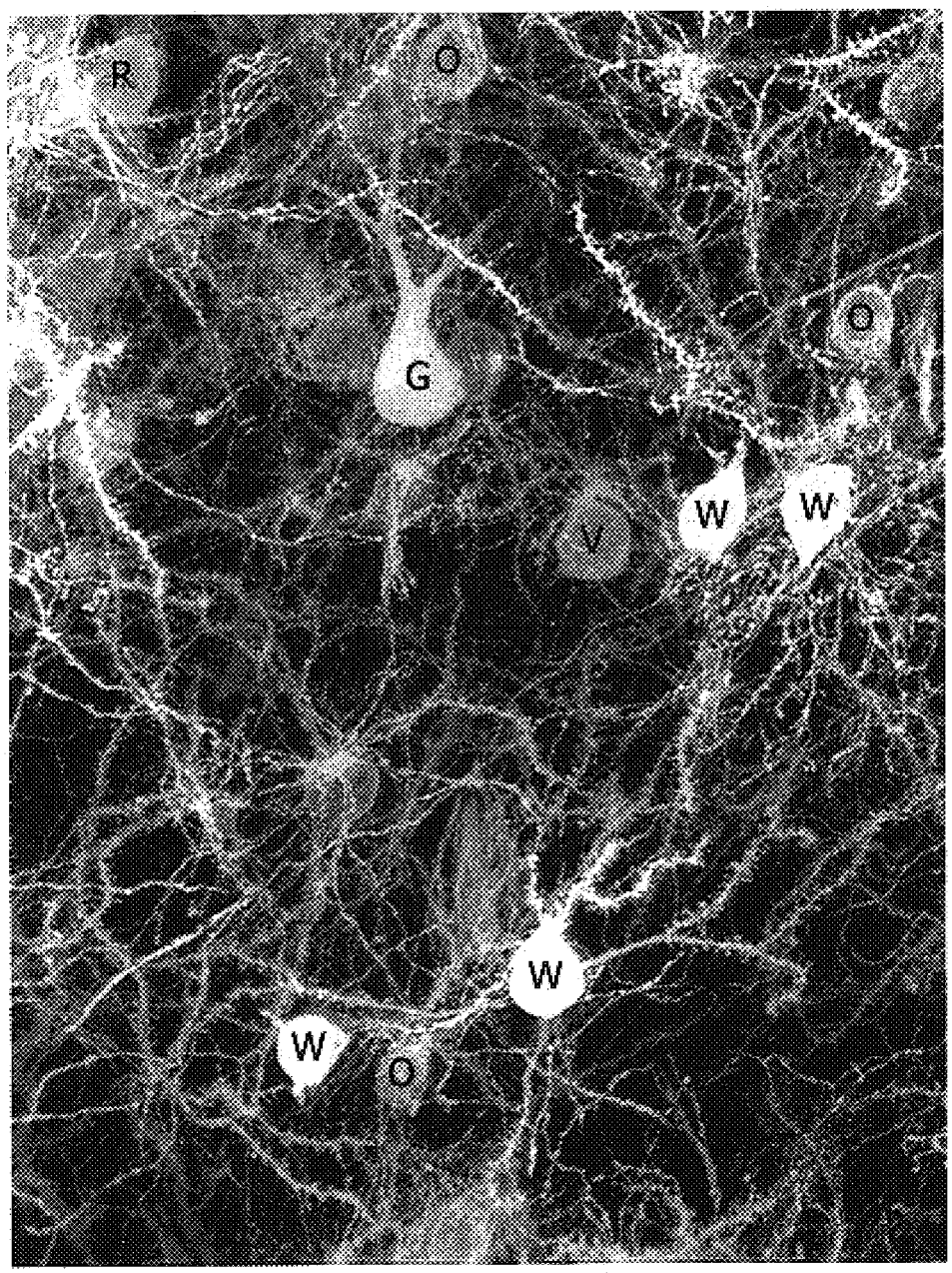
FIG. 1 is a photograph of labeled neurons in a fixed brain slice at high magnification, illustrating differentially labeled dendritic spines and axonal terminals when the present method is utilized. G=green, O=orange, R=red, V=violet, W=white

As used herein, "cell membrane" means any lipid bilayer, which surrounds a cell, cell compartment or organelle. Thus, the term is intended to include, but is not limited to, the outer membrane of the cell that surrounds the cytoplasm, the nuclear membrane and membranes surrounding cellular organelles such as the mitochondrial membrane.

As used herein, "fixed" means that a substance has been treated, usually with a protein denaturing solution, in order to preserve its morphology for cytological or histological examination. Thus, a "fixed" cell or tissue is a cell or tissue that has been preserved for cytological or histological examination.

As used herein, "coated" means that a film or layer of dye or other substance has formed around the particle or that the particle contains or is impregnated with a dye or other substance in sufficient quantities such that the dye or other material can be detected. It is not necessary that the film or layer be uniform. Thus, the term "coated particle" is intended to include, but is not limited to, particles having dye on the surface or internally incorporated.

As used herein, "animal" includes human beings.

As used herein, "voltage sensitive" dyes are dyes whose localization senses a difference in electrical potential across a cell membrane.

As used herein, "nucleic acid" dyes are dyes that stain nucleic acids such as DNA and RNA.

As used herein, "pH sensitive" dyes are dyes whose emission wavelength or intensity change in response to pH changes.

As used herein, "ion sensitive" dyes are dyes that exhibit changes in fluorescence when bound to a particular ion.

As used herein, "propel" or "propelling" means to move forward by the application of force.

As used herein, "particle" refers to an inert object, preferably spherical in shape, having sufficient structural integrity and mass necessary to acquire sufficient kinetic energy to function in the present method.

DETAILED DESCRIPTION

The following detailed description is provided to aid those skilled in the art in practicing the present method. Even so, this detailed description should not be construed to unduly limit the present invention as modifications and variation in the embodiments discussed herein can be made by those of ordinary skill in the art without departing from the spirit or scope of the present inventive discovery.

All publications, patents, patent applications and other references cited in this application are herein incorporated by reference in their entirety as if each individual publication, patent, patent application or other reference were specifically and individually indicated to be incorporated by reference.

The present method allows rapid labeling of individual cells with different dyes or dye combinations in both fixed and living cells and tissues. In physiological and biological research, as well as medical diagnosis, cell morphology often provides important information. The present method provides a means of rapidly labeling individual cells with multiple dyes. Such a method is useful for diagnosis during autopsies, surgical biopsies/frozen sections, necropsies, and the immediate diagnosis of diseases based on cell morphology, and permits enhanced diagnosis and study of neurological diseases, such as Alzheimer's disease. The current method is also useful for research relating to, e.g. chronic use of medication, mental illness and strokes.

The present method provides several advantages. First, the labeling of individual cells with dyes is rapid and complete, allowing, for example, the entire dendritic arbors of neurons to be labeled within minutes after dye-coated particles contact the cell membrane. In contrast to dye labeling, the GFP labeling technique requires many hours or days for GFP to be expressed in transfected cells (Lo et al., 1994, Neuron, 13:1263–1268.). The present method permits immediate study of tissues as soon as the preparation is made. The labeled tissues are able to be imaged in less than about one minute for living tissues and from less than about ten minutes to about thirty minutes for fixed tissues. Thus, the present method is less time consuming and less tedious than conventional methods. Such rapid labeling is especially useful in studying neuronal tissues such as brain slices due to their rapid deterioration after preparation. Second, in several embodiments, labeling involving passive dye transfer and diffusion independent of gene transcription and protein synthesis is provided. Thus, all types of cells can be labeled in both fixed and living tissues. In embodiments utilizing dyes, individual axons can be labeled without the necessity of the particles reaching the cell body as is required in other techniques. According to the present method, it is believed that the dye is released from the particle to diffuse along the cell's processes. Therefore, there is no need for the dye-coated particles to come into contact with the cell nucleus. Third, using various combinations of dyes or nucleic acid sequences encoding different fluorescent proteins, different neurons can be labeled at various non-overlapping excitation and emission profiles. Combined with high density labeling, this feature is potentially very useful in studying neuronal connections in complicated biological networks.

The various aspects of the present method are accomplished by a novel method that allows rapid and differential labeling of cells and tissues by contacting particles coated with dyes or nucleic acid sequences with the cells. In one embodiment, a particle coated with at least one dye is provided and the coated particle is propelled toward the target cell to cause the coated particle to contact the cell for a time sufficient to cause labeling of the target cell, generally its cell membrane. A number of dyes may be used including lipophilic dyes, voltage sensitive dyes, pH sensitive dyes, nucleic acid dyes, ion sensitive dyes, fluorescent dyes, protein binding dyes and combinations thereof. In one embodiment, a voltage sensitive or membrane potential dye is used. In another embodiment, carbocyanine dyes are used. In still another embodiment, calcium indicator dyes are used. Dyes can be used singly or in combination. When using multiple dyes, any combination of dyes may be used provided that the dyes do not have completely overlapping fluorescent emission profiles. By coating particles with various mixtures of dyes, individual neurons can be labeled at many different wavelengths and at controlled densities, thereby providing a useful method for anatomical and physiological studies.

The method of Singer et al., U.S. Pat. No. 5,573,909 requires that the coated particles be combined with a sample thought to contain the target materials and that an extended time be allowed to pass for the particles to form a complex with the target materials. After such time intensive complex formation, the sample is illuminated, resulting in fluorescence of the microparticles. The present method avoids this time intensive step. According to the present method, the coated particles are propelled toward the target cell or tissue. Thus, complete and rapid labeling is accomplished with a minimum of cell handling, cell preparation and cell disruption. Also, the present method provides illumination of the labeled cells or tissues at multiple excitation and emission profiles, which allows individual labeling of cells and cells contained in tissues. Previous methods did not produce differential labeling of neighboring cells, because such methods either labeled individual cells using dyes or nucleic acid sequences having a single excitation and emission peak, or groups of cells were labeled with dyes or nucleic acid sequences having multiple excitation and emission wavelengths. When multiple dyes or nucleic acid sequences are used according to the present method, cells are labeled individually with dyes or proteins having distinct emission profiles. When the labeled cells or tissues are imaged, the dyes or fluorescent proteins within individual cells emit light at differing emission wavelengths.

In accordance with the present method, particles coated with or containing at least one dye are propelled from an appropriate range, toward a target cell or group of target cells to cause the coated or impregnated particles to contact the target cells for a time sufficient to cause labeling of the target cell or group of target cells by release of the dye from the particle. A dye coated tissue or cell is formed, which may subsequently be imaged by detecting the presence of the dye and used for a variety of purposes including research and medical diagnosis.

The only physical limitation upon the particles is that they have sufficient mass to acquire the necessary kinetic energy to contact the cell membrane of the target cell to be labeled and that they have integrity sufficient to withstand the physical forces inherent in the process.

The size of the particles used can vary. Generally, the particles have a diameter greater than 0.7 microns. The particles may have a diameter between 0.3 microns to 4 microns. However, the larger the particle, the greater the resulting cell or tissue damage. In one embodiment, the particles have a diameter between about 0.7 microns and about 1.7 microns.

The particles can be made of various materials. Examples of suitable materials include ceramic, plastic, latex and metal particles. More particularly, examples of suitable inert particles include ferrite crystals, gold or tungsten spheres, and other metal spheres. Also, particles of high density, such as glass, polystyrene and latex beads may be used.

In one embodiment, the particles may be coated or impregnated with lipophilic dyes. In another embodiment, the particles are coated with ion sensitive dyes and in particular calcium indicator dyes. Particles may be coated with a single dye or with multiple dyes. When more than one dye is used, it is preferred that the dyes not have completely overlapping fluorescent emission profiles. Any lipophilic-hydrophobic dye may be used. Examples of useful lipophilic hydrophobic dyes include carbocyanine and voltage sensitive dyes. Likewise any calcium indicator dye can be used including dyes conjugated to large molecules such as dextran and esters of calcium indicator dyes.

Examples of suitable carbocyanine dyes include DiO (3,3'-dioctadecyloxacarbocyanine perchlorate), DiI (1,1'-dioctadecyl-3,3,3',3'-tetramethylindocarbocyanine perchlorate) and DiD (1,1'-dioctadecyl-3,3,3',3'-tetramethylindodicarbocyanine perchlorate) and combinations thereof. In preparations labeled with dyes having multiple emission profiles, the following dyes can be used: DiI exciting at 568 nm (red), DiO at 488 nm (green) and DiD at 647 nm (blue). These dyes are commercially available from Molecular Probes, Eugene, Oreg. Combinations of carbocyanine dyes may be used. Examples of combinations of carbocyanine dyes suitable for use in the present method include: 1 DiI: 1 DiO, 1 DiI: 1 DiD and 1 DiO: 1 DiD.

In one embodiment, voltage sensitive dyes that monitor membrane potential are used. These dyes are used to detect changes in voltage potential across a cell membrane. In one embodiment, changes in voltage potential are detected by the movement of the dyes between the inner surface and outer surface of the cell membrane. Particles coated with membrane potential dye or voltage sensitive dyes, therefore, are used where cell function is of interest. Any target cell suitable for use in the present method may be used.

In one embodiment, a method for determining changes in cell membrane potential is provided. At least one particle containing one or more voltage sensitive dyes is provided and propelled toward one or more target cells in order to contact the cell or the cell membrane for a time sufficient to cause labeling of the target cell by release of the dye from the particle. Any voltage sensitive dye may be used. Any changes in the dye are detected and correlated with changes in the cell membrane voltage potential. The voltage sensitive dye may or may not be a lipophilic dye. The target cell may be obtained postmortem. In one embodiment, a macroprojectile is used. In another embodiment, a macroprojectile stopping means such as a filter is also used.

Voltage sensitive dyes that are suitable for use in the present method include: di-4-ANEPPS (D-1199), di-8-ANEPPS (D-3167), di-2-ANEPEQ(JPW 1114)(D-6923), di-8-ANEPPQ(D-6925), di-12-ANEPPQ(D-6927), di-18:2-ANEPPS(D-6928), RH 795(R-649), RH 155 (R-1114), RGA-30(R-6922), N-(4-sulfobutyl)-4-(4-(4-(dipentylamino)phenyl)butadienyl)pyridinium, inner salt (Rh 421)(S-1108), N-(4-sulfobutyl)-4-(6-(4-(dibutylamino)phenyl)hexatrienyl)pyridinium, inner salt (RH 237)(S-1109), N-(3-triethylammoniumpropyl)-4-(4-(4-(diethylamino)phenyl)butadienyl)pyridinium dibromide (RH 414) (T-1111), N-(3-trimethylammoniumpropyl)-4-(4-(4-(diethylamino)phenyl) butadienyl)pyridinium dibromide (RH 461)(T-1113), WW 781, triethylammonium salt (W-435), bis-(1,3-diethylthiobarbituric acid)trimethine oxonol (DiSBAC$_2$(3))(B-413), bis-(1,3-dibutylbarbituric acid)pentamethine oxonol (DeBAC$_4$(5))(B-436), bis-(1,3-dibutylbarbituric acid)pentamethine oxonol (DiBAC$_4$(3)) (B-438), 3,3'-bis-(3-sulfopropyl)-1,1'-diethyl-5–5', 6,6'-tetrachlorobenzimidazolylcarbocyanine, potassium salt (TDBC-3)(B-6952), 3,3'-bis-(4-sulfobutyl)-1,1'-diethyl-5,5', 6,6'-tetrachlorobenzimidazolycarbocyanine, potassium salt (TDBC-4)(B-6953), 1,1',3,3,3',3'-hexamethylindocarbocyanine iodide (DiIC$_1$(3))(H-379), 1,1',3,3,3',3'-hexamethylindocarbocyanine iodide (DiIC$_1$(3))(H-379), 1,1',3,3,3', 3'-hexamethylindodicarbocyanine iodide (DiIC$_1$(5))(H-14700), mercocyanine 540 (M-299), oxonol V (bis-(3-phenyl-5-oxoisoxazol-4-yl)pentamethine oxonol)(O-266, oxonol VI (bis-(3-propyl-5-oxoisoxazol-4-yl)pentamethine oxonol)(O-267), 1-pyrenebutyltriphenylphosphonium bromide(PyTPP$^+$)(P-6921), rhodamine 123(R-302), tetramethylrhodamine, methyl ester, perchlorate (TMRM)(T-668), tetramethylrhodamine, ethyl ester, perchlorate (TMRE)(T-669), 5,5',6,6'-tetrachloro-1,1',3,3'-tetraethylbenzimidazolylcarbocyanine iodide (JC-1; CBIC$_2$(3))(T-3168) and any combination thereof. Previously, access to the membrane has proven difficult in this type of research. Additional dyes or other substances, such as oxanols, may be attached to the particles by the same methods used in the present invention.

In an additional embodiment, a method for determining intracellular calcium concentrations or changes in such concentrations is provided. In this embodiment, particles are coated with dyes that report intracellular calcium concentrations or changes in intracellular concentrations (calcium indicator dyes). Numerous calcium indicator dyes are known in the art and are available from commercial sources such as Molecular Probes Inc., Eugene, Oreg. and include their salts (e.g. potassium salts), derivatives (e.g. nitro derivatives) analogs (e.g. fluorinated analogs), and conjugates (e.g. dextran conjugates). In general such dyes include those of the Fura and Rhod series. Specific, but non-limiting examples of available calcium indicator dyes include Fura-2, Fura-4F, Fura-5F, Fura-6F, Fura-FF, Fura-Red, Fura-2 dextran, Indo-1, Indo-5F, Benzothiaza-1, Benzothiaza-2, Fluo-3, Fluo-4, Fluo-5N, Fluo-5F, Fluo-4FF, Rhod-2, X-Rhod-1, Rhod-5N, X-Rhod-1, X-Rhod-5N, Rhod-5F, Rhod-FF, X-Rhod-5F, X-Rhod-FF, Oregon Green® Calcium green, Calcium orange, and Calcium crimson.

A method for measuring membrane fluidity is also provided. In this variation, the movement of the dye in the membrane as a function of time is measured. Again, any dye suitable for use in the present method may be used. In one embodiment, a lipophilic dye is used.

Alternatively, the labeling techniques may employ multiple particles containing a plurality of nucleotide sequences encoding fluorescent proteins with each of the fluorescent proteins having a different emission spectrum. The plurality of particles is propelled toward the cells to cause the particles to enter the cells and reside in the interiors of said cells. In one embodiment, each particle contains nucleic acid sequences encoding only a single fluorescent protein, but particles containing sequences encoding different fluorescent proteins are present in the population of particles. In another embodiment, individual particles contain nucleic acid sequences encoding multiple flourescent proteins with each of the proteins having a different emission spectra. Various nucleotide sequence encoding fluorescent proteins can be used. Examples of useful fluorescent proteins such as those with different emission spectrum include red fluorescent protein, green fluorescent protein and variants of green fluorescent protein such as yellow, cyan and blue (Tsien, 1998, *Ann. Rev. Biochem.*, 67:509–544; Chalfie and Kain, *Green Fluorescent Protein: Properties, Applications, and Protocols*, Wiley-Liss, 1998; Matz et al., 1999, *Nature Biotech.*, 17:969–973).

Particles may be coated with dye by any method known in the art. Generally, the dye is non-covalently absorbed onto the surface of the microparticles. For example, particles can be coated with dye by precipitation, evaporation or drop by drop. Evaporation is one suitable method of coating the particles. Generally, particles ranging in size from 0.6 to 1.7 um are spread evenly onto a flat surface, for example a glass slide. The amount of particles used can vary, but is generally about 150 mg. For example, a solution containing an organic solvent and a lipophilic dye may be added incrementally to the particles on the flat surface so that the solution can be spread evenly on the flat surface as close to a monolayer as possible. In one embodiment, the solution contains about 300 µl methylene chloride and 10 µg lipophilic dye. The dye/organic solvent solution is added about 30 µl at a time onto the particles. However, the composition of the final solution can vary. As the organic solvent is allowed to evaporate, the dye precipitates to form a very fine layer of particles. When the evaporation is complete, the particle layer is scraped from the flat surface and transferred to a tube to be re-suspended in distilled water or other aqueous solution. The suspension is mixed with a vortex mixer and then sonicated to prevent the formation of clusters of particles. When the particles are to be propelled using a particle gun, the solution containing the particles can be introduced into a plastic tube that is compatible with the particle gun, and the particles are allowed to precipitate to the bottom of the tube. Thereafter, the supernatant is removed, preferably with a syringe, and the tube containing the particles is allowed to air dry. It is not required that the tube dry completely.

Similarly, any known method of precipitation may be used. For example, with a lipophilic dye, the dye is dissolved in an organic solvent solution and the particles are added to the solution. Subsequently, distilled water is added to the organic solvent-particle mixture. This causes the dye to precipitate. Some of the precipitated dye will contact the metal particles and attach to them. The particles are then allowed to settle, the supernatant removed, and the particles dried. It is not necessary that the particles dry completely.

In one embodiment, polyvinylpyrrolidone (PVP) is added to the solution prior to evaporation or precipitation to cause particles to attach to the tube in a more uniform manner. The amount of PVP added to the solution can generally vary from about 0.001 mg/ml to about 10 mg/ml of PVP.

In another embodiment, particles are coated with dyes or other substances using a drop by drop method. According to this method, the dye or other substance is placed incrementally onto the particles until the particles are completely covered by the dye. Evaporation of the solvent must take place after each drop so that no excess accumulation of solution occurs on any area of the particles. Care is also taken so that the particles are not over immersed in the dye. Over immersion is noticed when the color of the particle starts to change from its natural color, for example gray for tungsten particles, to the color of the dye in use. A color change indicates that the final amount of dye to be added has been reached. This step is important because over immersed particles form clusters, which are not desirable when labeling single cells.

Any solvent in which the dye is miscible may be used for introducing the dye onto the particle. Examples of suitable solvents for lipophilic dyes include ethanol, dimethyl sulfoxide and methylene chloride. Macroprojectiles are comprised of a plurality of particles coated or impregnated with dye. They can be prepared with particles having similar individual excitation and emission profiles or with particles having differing excitation and emission profiles, or both. Generally macroprojectiles are formed by coating the inner surface of a length of hollow tubing with dye-coated particles. Any tubing may be used. In one embodiment plastic tubing is used. One example of suitable plastic tubing is commercially available from Bio-Rad Laboratories, Philadelphia, Pa. (Cat#165-2441, 1999 Catalogue). An aqueous suspension of dye coated particles and water is formed by mixing with a vortex mixer and sonicating the dye coated particles, prepared as previously described, in water or other aqueous medium to break up clusters of particles. Where multiple dyes are used, the individually colored particles are combined to form the suspension. A length of tubing is placed horizontally and filled with the aqueous suspension of dye-coated particles. The particles are allowed to settle to the bottom and the supernatant is removed, typically with a syringe. The tubing is then dried and cut into pieces. It is not necessary that the tubing be dried completely. In one embodiment, the tube is rotated during drying in order to more evenly distribute the particles. In one embodiment, the "Tubing Prep Station" included in the "Helios Gene Gun System," available from Bio-Rad Laboratories, Philadelphia, Pa. (Cat#165-2431, 1999 Catalogue) may be used. Following drying, the tubing is cut into lengths suitable for the particular particle gun or other ballistic device used.

According to the present method, the particles can be propelled by any method suitable for accelerating small particles, provided that it is capable of propelling the particles to a specific target at a predetermined velocity. For example, the particles may be propelled by a gas means. An example of a suitable gas means is a biolistic "gene gun" or "particle gun" described in U.S. Pat. No. 4,326,524 to Drake, Jr. et al. (1982, incorporated by reference. However, any gas means or other accelerating method may be used. In one embodiment, the "Helios Gene Gun System," available from Bio-Rad Laboratories, Philadelphia, Pa. (Cat#165-2431, 1999 Catalogue) is used. The mechanical impulse method, centripetal method and electrostatic method may also be used for propelling the dye coated particles, and are described in U.S. Pat. No. 5,036,006 to Sanford et al. (1991), herein incorporated by reference. A process that uses any accelerating method which operates on the above principles or other principles which accomplish the same result. The structural details of any specific apparatus can vary from those specifically discussed herein as can be perceived by one skilled in the art of acceleration devices.

In some instances, it may be advantageous to utilize a macroprojectile stopping means when practicing the method. The macroprojectile stopping means is generally interposed between the coated or impregnated particles and the target cell or group of target cells. A macroprojectile stopping means is any object, material, or substance that stops a macroprojectile while allowing at least one coated particle to continue toward the target cells or tissues. In one embodiment of the present method, the macroprojectile stopping means is caused to contact a macroprojectile before the macroprojectile contacts the target cell. The use of a macroprojectile stopping means is not essential to practice the present method. When using biolistic labeling, however, the use of a macroprojectile stopping means may produce improved results. Specifically, the macroprojectile stopping means prevents the clustering of particles onto the target cells or tissues. Thus, the coated particles are more evenly distributed onto the target cells or tissues and able to be more distinctly imaged. The macroprojectile stopping means may be any commercially available filter. Where a filter is used, preferably, the filter is a very thin membrane and has a uniform distribution of single channels such that the particles are layered uniformly onto the cell or tissue. The filter can be made of any substance. The material of the filter should be thin, but strong enough to withstand air pressures that are typically between 50 to 200 psi. The pore sizes should be of a diameter slightly bigger than the desired particle size. Preferably, the pore density of the filter is high. In one embodiment, a pore diameter of 1 to 8 microns is used, as are track-etched membrane filters. A membrane filter with 3 µm pore diameter and $8.0 \times 10^5$ pores/cm$^2$ pore density may be used. An example of a suitable commercially available membrane filter is a Falcon® cell culture insert that may be obtained from Becton Dickinson Labware, N.J. Other filters may also be used. Other examples of suitable filters include: cell culture inserts: 24-well plate description with 1.0 µm pore size (Fisher Scientific, Pa., Cat. No. 08-774-157, B-D (Becton Dickinson) No.: 40569), 6-well plate description with 3.0 µm pore size (Fisher Scientific, Pa., Cat. No. 08-774-158 B-D No.: 40573), 12-well plate description with 3.0 µm pore diameter (Fisher Scientific, Pa., Cat. No. 08-774-159 B-D No.: 40574), 6-well plate description with 8.0 µm pore diameter (Fisher Scientific, Pa. Cat. No.: 08-774-161 B-D No.: 40576), 24-well plate description: with 8.0 µm pore diameter (Fisher Scientific, Pa., Cat. No.: 08-774-162 B-D No.: 40578). If the membrane is attached to a frame, the frame is cut to a height of about 5 to 10 mm such that the filter is closer to the target cell or tissue (See FIG. 3). Placing the membrane closer to the target cell or tissue results in greater density of labeling.

Density of the labeling is also controlled by using various gas pressures or by changing the distance between the gun and the target cell or tissue. The distance between the gene gun and the target cell or group of target cells and the gas pressure are determined empirically and can be determined by one of ordinary skill in the art without undue experimentation. One advantage of the present method over conventional procedures is the ability to control the density of labeling. For example, when labeling a single cell, a low labeling density may be desirable, while when labeling complex biological systems such as brain tissue, a high labeling density may be preferred.

The distance between the target cell and the coated particle is generally between 2 mm to 15 mm, but may be between 2 mm to 4 cm; however, labeling may be accomplished at greater ranges. The closer the distance between the coated particle and the target cell or tissue, the greater the density and penetration of the particles. Conversely, when particles are propelled from greater distances from the target cell or tissue, the labeling is less dense. Unlike many conventional techniques, dense labeling is not troublesome, due to the ability of the present method to label individual cells with dyes having several distinct emission profiles. When particles are propelled by the biolistic method, the gas pressure at which the particle gun is operated affects the depth of labeling. Lower gas pressures and larger distances between the gun and the target cell or tissue results in lower labeling densities. In one embodiment, 60–120 psi Helium gas is used. It is believed, however, that the most reliable way of controlling the density of labeling is by the use of filters and varying the particle content of the macroprojectile until the desired density is achieved. In general, the higher the particle content of the macroprojectile and pore density of the filter, the higher the density of labeling. Shooting the target cell or tissue several times is also useful to increase the labeling density. Multiple shootings, however, may lead to injury of a living target cell or tissue.

Figure 3A:
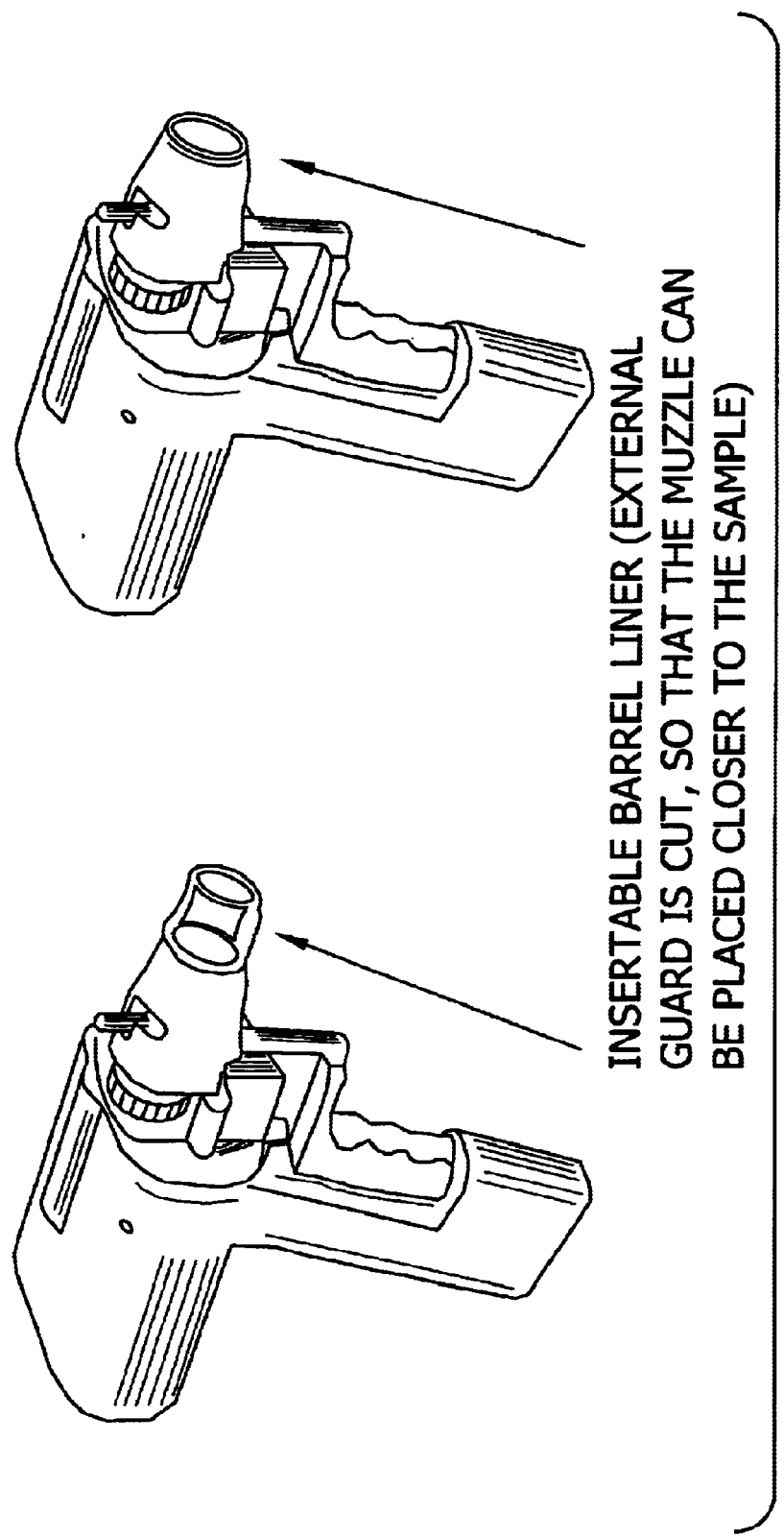
FIG. 3A is an illustration of a gene gun altered to enable greater labeling density.

Applicants' experimental results suggest that superior labeling generally occurs when the particles are propelled deep into a tissue or group of cells. In one embodiment, the coated particles are propelled about 50–70 µm into the target cell or target tissue. In another embodiment, coated particles are propelled 50–100 µm into the target cell or target tissue. Where the propelling device is a particle gun, the density in which the particles are propelled into the tissue may be increased by removing the nozzle of the particle gun, thereby decreasing the distance between the gun and the target cell or tissue (FIG. 3).

In the present method, labeling is accomplished with a minimum of cell handling, cell preparation, or cell disruption. It is not necessary that a coated particle reside on a particular cell or tissue. In one embodiment, labeling occurs when the dye or nucleotide sequence diffuses into the cell membrane of the target cell. Labeling is almost instantaneous. The labeled cells or tissues may be imaged in less than about one minute for living cells and tissues, and in less than about five minutes to about thirty minutes for fixed cells and tissues. The time between propelling of the particle and imaging can be increased to produce optimal imaging results. Further, a target cell may be labeled with at least one additional dye by a means other than a dye coated particle before or after the target cell has been labeled by the present method. In one embodiment, after the target cells or tissues are labeled, they are washed to remove any particles that fail to properly contact the tissue or cell.

Using the present method, the cell type, size, shape, presence or absence of a cell wall, cell number, or cellular environment does not significantly alter effectiveness. Examples of the wide array of cells which can be subjected to this method include animal cells, microbial cells, and plant cells. The target cells may be intact living cells or fixed cells. The cells may be individual cells or part of a tissue. Examples of the wide array of animal tissue that the present method may be used to label include tumor tissue, epidermal tissue, muscle tissue, bone marrow tissue, neural tissue and organ tissue. Brain tissue and human biopsy tissue may also be labeled according to the present method. Further, the target cell or tissue may be obtained post mortem. The present method produces a dye labeled tissue in which the individual cells are differentially labeled and able to be imaged using any suitable detection method. When multiple dyes are used, the tissue is typically labeled with at least two dyes having emission profiles that are not completely overlapping. In one embodiment, the tissues comprise cells individually labeled with a majority of adjacent cells containing dyes with different emission spectra. In another embodiment, the cells of the tissue are labeled with lipophilic dyes, pH sensitive dyes, nucleic acid dyes, ion sensitive dyes, protein binding dyes, voltage sensitive dyes or any combination thereof. In a further embodiment, the dyes include at least one lipophilic or voltage sensitive dye. In still another embodiment, the dyes are carbocyanine dyes. The number of labeled cells the in tissue can vary over a wide range. In one embodiment, the tissue contains at least 25 labeled cells. In another embodiment, the tissue contains at least 50 labeled cells and in still yet another embodiment the tissue contains at least 100 labeled cells. All of the cells within the tissue that are adjacent to each other need not contain dyes or combination of dyes with different emission spectra. In one embodiment, however, at least 50% of adjacent cells contain dyes or combination of dyes with different emission spectra. In another embodiment, at least 75% of the adjacent cells contain dyes or combinations of dyes with different emission spectra. In still another embodiment, at least 90% of adjacent cells contain dyes or combinations of dyes with different emission spectra.

Any suitable method may be used to detect dyes in a labeled target cell. In one embodiment, microscopy is used to detect a labeled target. Labeled target cells can be detected using a fluorescence microscope, a multiphoton microscope or a confocal microscope. In one embodiment where microscopy is used to detect the presence of the dye, the method further comprises using a computer aided image analysis system. Target cells or tissues labeled with multiple dyes may be illuminated simultaneously or sequentially. Specifically, it is advantageous to expose the target cells or tissues to one excitation wavelength at a time. In one embodiment, the image of the cells is recorded. The cells' image may be recorded chemically or digitally and may or may not be permanent.

In one embodiment, the present method can be used to diagnose a disease, disorder or condition. In contrast to other methods, it is not necessary that the target cells or tissues be removed from the body. Animal cells or tissues may be labeled and imaged in situ. The target cells or tissue may be contacted with the coated particles and imaged without disrupting the surrounding tissue or cells. A disease, disorder or condition that is characterized by a change in cell morphology, membrane potential or other parameter that can be detected by staining may be diagnosed according to the present method. Examples of such diseases, disorders and conditions include Alzheimer's disease, certain cancers, mental illnesses or diseases, strokes and illnesses caused by chronic use of medication.

In another embodiment, the present method can be used for studying the morphology of a cell. The dyes may be any dyes suitable for use in the present method, for example, lipophilic dyes.

In a further embodiment, the present method can be used to monitor a physiological process in a cell. According to the present method at least one particle containing at least one dye that is sensitive to a physiological process is provided and propelled toward a living target cell to cause the coated particle to contact the cell for a time sufficient to cause labeling of the target cell by release of the dye from the particle. After labeling, changes in the dye are detected, and the changes correlated with changes in physiological process within the target cell. The dye may be any dye suitable for use in the present method, including dyes that are sensitive to a physiological process such as, pH sensitive dyes, voltage sensitive dyes and ion sensitive dyes.

EXAMPLES

The following examples are intended to provide illustrations of the application of the present method. The following examples are not intended to completely define or otherwise limit the scope of the invention.

Example 1

Labeling Cells with Lipophilic Dyes 1.1 Preparation of Particles

Ten $\mu$g of DiI, DiO and DiD (Molecular Probes, Cat#D-282, D-275, D-307) were individually dissolved in 300 $\mu$l methylene chloride to make stock solutions for each dye. Various proportions of different dyes were mixed to make 7 different preparations as follows: (a) DiI; (b) DiO; (c) DiD; (d) 1 DiI: 1 DiO; (e) 1 DiI: 1 DiD; (f) 1 DiO: 1 DiD; (g) 1 DiI: 1 DiO: 1 DiD.

Generally, approximately 50 mg of tungsten particles ranging in size from 0.6 to 1.7 um were spread evenly on a glass slide. A solution containing methylene chloride and a stock solution of lipophilic dye was added to the particles on the flat surface so that the solution spread evenly on the flat surface as close to a monolayer as possible. As the methylene chloride was allowed to evaporate, the dye precipitated to form a very fine layer of tungsten particles. The particle layer was then scraped from the flat surface and transferred to a tube to be re-suspended in water or other aqueous solution, mixed with a vortex mixer and sonicated to prevent the formation of large clusters of particles.

1.2 Tissue Specimens

Neonatal CF-B mice were obtained from a breeding colony (Harlan/Sprague-Dawley). The date of birth was designated postnatal day 0 (P0). Mouse pups were anesthetized with 0.2 ml sodium pentobarbital and the perfused with 4% paraformaldehyde. Brains were removed and postfixed in 4% paraformaldehyde for 1 hour and then section with a vibratome (200–300 $\mu$m thick).

For labeling in living animals, neonatal mice at P6 were anesthetized by chilling in ice until movement ceased. The skull was exposed by a midline skin incision. A craniotomy was performed to expose a small window (about 3 mm in diameter) over the parietal cortex and the dura in this region was removed. After delivering dye coated particles through the small window, the animal was anesthetized with 0.2 ml sodium pentobarbital and the perfused with 4% paraformaldehyde.

Neuronal cultures were prepared by dissociation of the lateral cortex or hippocampus as described by Craig et al. (*Neuron* 10: 1055–1068, 1993) and Rose et al. (*Methods in Toxicol*. Vol 1A, pp 46–60, 1993) and fixed with 4% paraformaldehyde prior to labeling. Human brain tissue was obtained from an autopsy specimen fixed for 48 hours in 4% paraformaldehyde and section on a vibratome prior to labeling.

Fetal mouse brains (E14) were removed, dissected, and fixed with 4% paraformaldehyde. To label a distinct population of early cortical cells whose process terminate at the pial surface, the particles were delivered to the pial and allowed to retrogradely label the cell bodies prior to vibratome sectioning.

1.3 Cell Labeling

Dye coated particles were delivered to the preparation using a commercially available biolistic device or "gene gun" (Bio-Rad, Helios Gene Gun system, catalog no. 165-2431). A membrane filter with a 3 $\mu$m pore size and $8.0 \times 10^5$ pores/cm$^2$ density (Falcon cell culture inserts no. 3096, Becton Dickinson Labware) was inserted between the gene gun and the preparation to prevent clusters of large particles from landing on the tissue. Density of labeling was controlled by using various gas pressures (60–120 psi helium gas) or by changing the distance between the gun and the preparation (5–15 mm). Lower gas pressures and larger distances between the gun and the tissue lead to lower densities. The most reliable way of controlling the density of labeling appeared to be the use of filters and varying the particle content of the bullets until the desired density was achieved. Shooting the tissue several times (up to four) was also useful to increase the labeling density although it may lead to more injury with live tissue.

1.4 Imaging

A confocal microscope having a long-distance water-immersion objective 60×, 0.9 NA or 60×1.4 NA oil immersion objective was used to image the preparations. In preparations labeled with multiple dyes, the particles were labeled with dyes having the following emission profiles: DiI labeling at 568 nm (red), DiO at 488 nm (green) and DiD at 647 nm (blue). Scanning the specimens either sequentially or simultaneously using the three excitation lines in the Kr-Argon laser with three separate barrier filter sets (522+/−18 nm for DiO, 590+/−20 nm for DiI, and 680+/−16 nm for DiD) gave good separation of the three image planes.

1.5 Results

In living tissues, neuronal dendritic trees and glial cells appeared fully labeled almost immediately (<5 minutes) after particles contacted the tissue (FIG. 1). Labeled dendritic arbors and axons of passage could be followed for hundreds of micrometers. In order to determine the speed of labeling, P20 live retinal explants were shot with dye coated particles and imaged at various intervals at room temperature. Two minutes after particle delivery, multiple cell bodies and almost complete dendritic labeling were apparent. At 5 minutes, complete dendritic labeling was seen. At 10–15 minutes, well-labeled axons were observed entering the optic nerve 150–200 μm away from the initial labeling sites. At 1.5 hours, axons up to 400 μm from the labeling site were visible. Similar labeling rates were also observed in living brain slices from adult mice. These observations give an apparent diffusion coefficient of about $10^7$ cm$^2$/s. To compare the speed of labeling in fixed tissues, dissociated hippocampal neurons in culture and paraformaldehyde fixed retinal explants were used. In both cases, the speed of dye diffusion was several fold slower, and it appeared that the diffusion time was slower in proportion to the strength and time of fixation.

Typically, only one dye coated particle juxtaposed to the cell membrane or the soma, or a branch of the dendritic or axonal arbor of a labeled cell was observed, indicating that cell labeling does not depend on the location of the particle in contrast to the requirement for perinuclear labeling with gene coated particles (Lo et al., 1994, *Neuron*, 13:1263–1268).

To explore the possibility of labeling neighboring neurons with different colors, the appearance of various individual lipophilic dyes and dye combinations was tested. Using three excitation/emission profiles as the red (for DiI), green (for DiO), and blue of (DiD) channels, respectively, of fall color (24 bit) images, it was possible evaluate the emission spectra of neurons labeled with particles that were coated with various combinations of the three lipophilic dyes. For example, bombardment of tissue with particles coated with both DiO (green) and DiI (red) yielded labeled neurons that appeared yellow or orange. Furthermore, when particles were coated with equal concentrations of DiI, DiO and DiD, many neurons were strongly labeled in all three channels and hence appeared white. It was also found that particles coated with other combinations of the three dyes (e.g. 2 parts DiI to 1 part DiO to 1 part DiD) gave yet other colors, suggesting that a large number of different colors could be obtained.

Using the present method it was possible to label individual neurons in different colors in a fixed cortical brain slice by loading the gene gun with a mixture of particles coated with seven different combinations of dyes. At high magnification, neurons and their processes, including dendritic spines, appeared completely labeled. Although the labeling density was very high, the precesses were easily distinguished from each other due to the variety of colors. Multicolor labeling also allowed the simultaneous imaging of pre- and post-synaptic components of developing and mature circuits.

It was also possible to label cortical neurons in vivo by delivering the particle through a small hole in the cranium. The composition and morphologies of the cells in the fetal brains could also be rapidly assessed. Fixed brain sections obtained from human autopsy material were also well labeled. It was possible to completely label the dendritic arbor of individual cells such as Purkinje cells in the cerebellum of the mouse. Cell types other than neurons were also labeled.

Example 2

Labeling Cells with Calcium Indicator Dyes 2.1. Preparation of Particles

To prepare calcium indicator-coated particles, a small amount (50 mg) of gold or tungsten particles (1.0–1.3 μm diameter, Bio Rad) was place onto a clean glass slide. One mg of calcium indicator dye (Calcium Green-1, Oregon Greene® 488 or Fura-2 conjugated to 10,000 MW dextran; Molecular Probes, Eugene, Oreg.) was dissolved in 20–40 μl of distilled water and the solution throughly mixed with the particles on the slide. The indicator coated beads were spread uniformly across the glass slide, air dried, and then scraped off into a clean tube. To prevent clumping, the particles were sonicated in 200 μl of methanol for 15 minutes. Methanol was then added to 1 ml, the beads vortexed, and the lighter particles removed for use while the heavier particle clusters were discarded. The vortexing was then repeated. Following vortexing, the particles were resuspended in 9 ml of methanol. "Cartridges" were prepared by injecting the vortexed solution into three, 25 inch pieces of plastic tubing (Bio Rad catalog no. 165-2441) coated with 10 mg/ml PVP in ethanol (Bio Rad catalog no. 165-2440). The particles were then allowed to settle onto the tube wall for 5 to 15 minutes (depending on the desired density) before the remaining liquid was slowly withdrawn. The particle coated tube was air dried or in a gentle stream of nitrogen gas and cut into 13 mm pieces. "Cartridges" were stored for short periods of time at room temperature. For longer storage, "cartridges" were stored in a container with desiccant at 4° C.

2.2 Tissue Specimens

Six month old mice were anesthetized with 0.2 ml sodium pentobarbital and then decapitate. Brains were rapidly removed and quickly sectioned at 300 μm with a vibratome in chilled lactated Ringer's solution superfused with 95% $O_2$ and 5% $CO_2$. Brain slices were kept in bubbled Ringer's solution at room temperature prior to imaging and at 34° C. in a recording chamber during imaging.

2.3 Cell Labeling

Labeling of the cells, was as described in Example 1. Brain slices were placed onto nitrocellulose filter paper (Millipore, Bedford, Mass., catalog no. 9004-70-0), transferred to 35 mm culture dishes and maintained alive in oxygenated Ringer's solution. Just prior to labeling, excess fluid on the tissue was quickly removed and the dye coated particles propelled into the tissue using a Bio-Rad Helios Gene Gun. To protect the tissue from particle clusters and the shock wave from the gene gun, a membrane filter 3 μm pore size and $8.0 \times 10^5$ pores/cm$^2$ density was placed between the gun and the tissue preparation as in Example 1. Immediately after shooting, the tissue was washed and then continuously superfused with oxygenated Ringer's solution to minimize background labeling by dye spread outer surface of the slice, and to ensure that the slices remained healthy.

2.4 Imaging

Images were obtained using a confocal microscope as in Example 1 (488 nm excitation line, 522+/−35 nm barrier filter) or using a low light level camera imaging system (Wong et al., 1998, *J. Neurosci.* 18:8839–8852).

2.5 Results

About 1 minute after particle delivery, cell bodies and dendrites were labeled with the calcium indicator. Dendritic filling occurred in a subset of cells within several minutes and continued over time. How quickly entire dendritic arbors were filled depended on the size of the cells and the density of indicator on the particle. In some cells, complete filing occurred with minutes after shooting. Typically, only one particle was observed within each cell body, however, particles landing within neuronal processes sometimes resulted in labeling many nearby cell somata (5–10 cells) and their processes, suggesting that indicator loading can occur retrogradely through neuronal processes.

The labeling efficiency was variable and dependent on factors such as cartridge particle density, gene gun pressure, and distance of the nozzle from the tissue. For example, in order to obtain a density of 15 labeled cells/mm$^2$ in the hippocampal CA1 region containing mainly pyramidal neuronal somata, delivery of approximately 100–200 particle/mm$^2$ was required. This was accomplished by shooting the tissue once at 180 psi through the membrane filter. Cell somata labeled were generally located 20–50 $\mu$m within the tissue although sometimes cells deeper in the tissue could be loaded. Because each particle probably carried varying amounts of indicator, the intensity of labeling varied from cell to cell.

Example 3

Effect of Dye Labeling on Cell Viability 3.1 Tissue Specimens

To determine whether the labeling procedure affects the physiology of cells in living tissue, the spontaneous activity and response of labeled neurons to exogenous glutamate was monitored. Retinae were isolated from embryonic chicks. Retinal whole mounts were prepared for calcium imaging by the method utilized in Wong et al., 1998, *J. Neurosci.*, 18:8839–8852.

3.2 Cell Labeling and Imaging

Briefly, the retinae were loaded with Fura-2 dye commercially available from Molecular Probes Inc., Eugene, Oreg. by incubation for an hour in 10 $\mu$M Fura-2AM in 0.001% pluronic acid in chick Ringer's solution. Chick Ringer's solution is comprised of 2 mmol $CaCl_2$, 5 mmol KCl, 2 mmol $MgCl_2$, 124 mmol NaCl, 1.25 mmol $KH_2PO_4$, 20 mmol glucose and 20 mmol HEPES ((N-[2-Hydroxyethyl] piperazine-N'-[2-ethanesulfonic acid]). Spontaneous and evoked activity was recorded from the Fura-loaded retinae maintained in oxygenated Ringer's solution at 35° C. using the Bio-Rad Multi photon system, available from Bio-Rad Laboratories, Philadelphia, Pa. (MRC-1024 m) following particle delivery by the present method. The temperature was monitored by placing the Ringer's solution on a heated stage equipped with a thermostat. The excitation wavelength was set at 775 nm. Images of a Fura-2 labeled field containing several dye-labeled cells (256×256 pixels) were acquired every 3 seconds before and during bath application of 100 $\mu$M glutamate using a fluorescence microscope. Changes in intracellular calcium levels $[Ca^{2+}]_I$ were detected by changes in the intensity of fluorescence (increase in $[Ca^{2+}]_i$ reported by a decrease in fluorescence). After Fura-2 recordings, switching to the confocal mode of the microscope allowed capture of the morphology of dye-labeled cells within the same field. Switching between two-photon and confocal scanning did not alter the position of the labeled cells within the field of view and thus enabled alignment of the dye-labeled cells with Fura-2 labeling. To observe dynamic changes in dendritic structure, a time-lapse movie of dye-labeled processes was obtained. Images of the processes were acquired every 5 seconds, with the confocal aperture set to the fully open position so that processes which move in and out of focus could be distinguished from those that remain in the focal plane.

3.3 Results

Figure 2D:
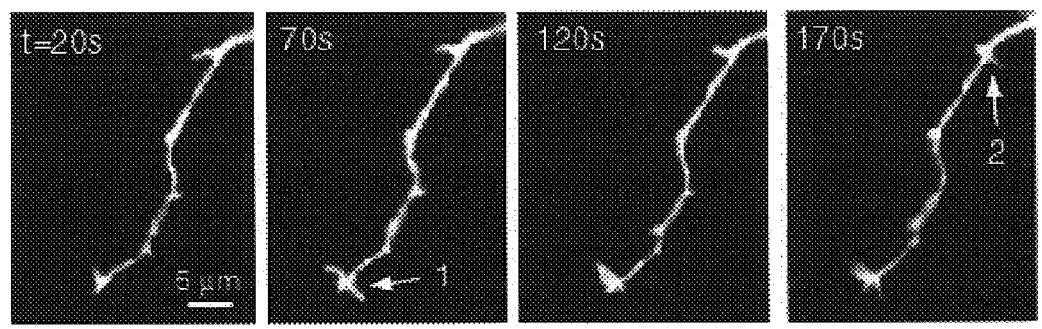
FIG. 2D is a set of time-lapse confocal images of an E12 chick retina ganglion cell illustrating structural changes in the dendritic process of an E12 chick retina ganglion cell after labeling using the present method. Dendritic processes in neurons undergo structural change during development as observed in earlier studies with neurons labeled using GFP (Wong et al., Soc. Neuro. Abst. 1998; 24:1766; Dunaevsky et al., *Proc. Natl. Acad. Sci. U.S.A.*, 1999, 96:13438–13443). These images show that these structural changes are also prominent in developing neurons labeled using the present method.
Figure 2E:
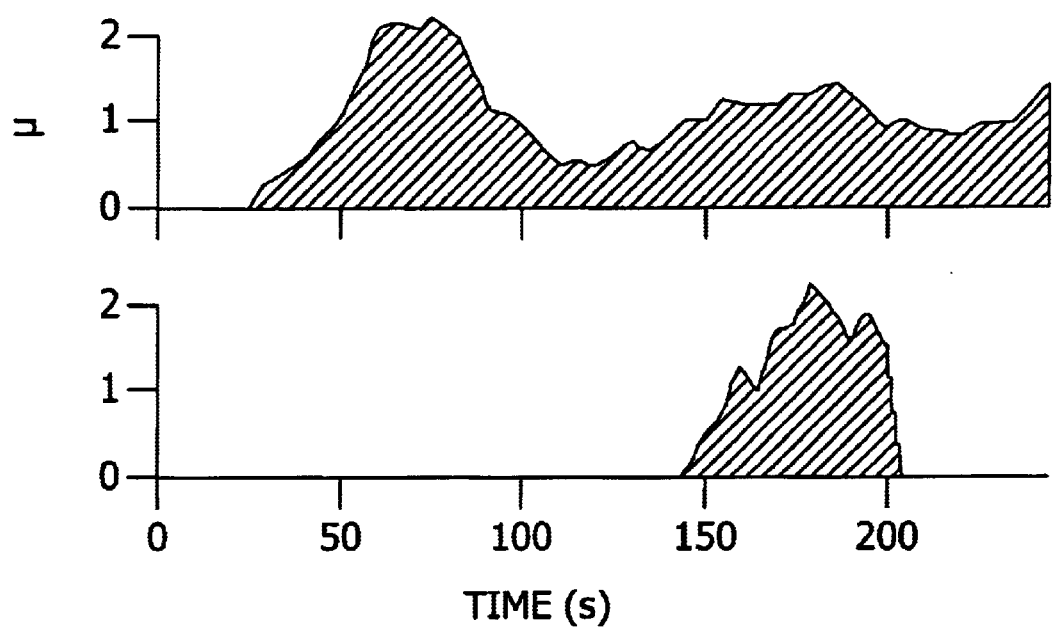
FIG. 2E is a graph of the behaviors of small processes 1 and 2 over time. The graph quantitates the changes in length in dynamic processes 1 and 2.

FIG. 2 shows the physiological effect of cells in living tissue using the present method. The dye labeled retinal cells were spontaneously active and responded to glutamate. The responses of 2 cells to the application of glutamate as assessed by calcium imaging is plotted in FIG. 2E. Thus, cellular physiology appears unperturbed by the present method.

CONCLUSION

In light of the detailed description and the examples presented above, it can be appreciated that the several aspects of the invention are achieved.

It is to be understood that the present invention has been described in detail by way of illustration and example in order to acquaint others skilled in the art with the invention, its principles, and its practical application. Particular formulations and processes of the present invention are not limited to the descriptions of the specific embodiments presented, but rather the descriptions and examples should be viewed in terms of the claims that follow and their equivalents. While some of the examples and descriptions above include some conclusions about the way the invention may function, the inventors do not intend to be bound by those conclusions and functions, but put them forth only as possible explanations.

It is to be further understood that the specific embodiments of the present invention as set forth are not intended as being exhaustive or limiting of the invention, and that many alternatives, modifications, and variations will be apparent to those of ordinary skill in the art in light of the foregoing examples and detailed description. Accordingly, this invention is intended to embrace all such alternatives, modifications, and variations that fall within the spirit and scope of the following claims.

What is claimed is:

1. A method for individually labeling a cell within a population of cells whereby the cell is differentially labeled relative to neighboring cells within the population, the method comprising propelling a particle coated with a lipophilic hydrophobic dye at the population of cells to cause the particle to contact the membrane of the cell, and allowing the dye to diffuse into the cell membrane and thereby differentially label the cell relative to neighboring cells within the population.

2. The method of claim 1, wherein the lipophilic hydrophobic dye is a fluorescent dye.

3. The method of claim 2, wherein the fluorescent dye is a carbocyanine dye.

4. The method of claim 3, wherein the dye is selected from the group consisting of DiO, DiI, DiD, and any combination thereof.

5. The method of claim 1, wherein the propelling is by a gas mean.

6. The method of claim 5, wherein the gas means is a particle gun.

7. The method of claim 1, wherein the particle is a metal particle.

8. The method of claim 7, wherein the metal particle is selected from the group consisting of ferrite crystals, gold and tungsten.

9. The method of claim 1, wherein the population of cells is part of a tissue.

10. The method of claim 9, wherein the tissue is selected from the group consisting of tumor tissue, epidermal tissue, muscle tissue, bone marrow tissue, neural tissue, brain tissue, organ tissue, and human biopsy tissue.

11. The method of claim 9, wherein the coated particle is propelled 50–100 $\mu$m into the tissue to contact the membrane of the cell.

12. The method of claim 11, wherein the coated particle is propelled about 50–70 µm into the tissue.

13. The method of claim 1 wherein the labeled cell is a living or a fixed cell.

14. A method of imaging a cell, of claim 13, wherein the cell is labeled by the method wherein the labeled cell is a living cell and said cell is imaged within about one minute of the coated particle being propelled at the cell.

15. A method of imaging a cell, of claim 13, wherein the cell is labeled by the method wherein the labeled cell is a fixed cell and said cell is imaged within less than about five minutes of the coated particle being propelled at the cell.

16. A method of imaging a cell, wherein the cell is labeled by the method of claim 13, wherein the labeled cell is a fixed cell and said cell is imaged within less than about thirty minutes of the coated particle being propelled at the cell.

17. The method of claim 1, wherein the cell is a neuron.

18. The method of claim 17, wherein the particle contacts an axon.

19. The method of claim 17, wherein the particle does not contact the cell body.

20. A method for individually labeling cells within a population of cells whereby the cells are differentially labeled relative to neighboring cells within the population, the method comprising propelling a plurality of particles coated with one or more lipophilic hydrophobic dyes at the population of cells to cause the particles to contact the membranes of the cells, and allowing the dye to diffuse into the cell membranes and thereby differentially label the cells relative to neighboring cells within the population.

21. The method of claim 20, wherein the particles are coated with more than one lipophilic hydrophobic dye.

22. The method of claim 20, wherein one or more dyes the dye is a fluorescent dye.

23. The method of claim 20, wherein one or more lipophilic hydrophobic dyes has an emission profile that is distinct from each of the other lipophilic hydrophobic dyes.

24. The method of claim 22, wherein the fluorescent dye is a carbocyanine dye.

25. The method of claim 24, wherein the carbocyanine dye is selected from the group consisting of DiO, DiI, DiD, and any combination thereof.

26. The method of claim 20, wherein the plurality of particles is contained in at least one macroprojectile.

27. The method of claim 20, further comprising causing the macroprojectile to contact a macroprojectile stopping means before contacting the cells, the macroprojectile stopping means being capable of stopping the macroprojectile while allowing at least one of the plurality of particles to continue toward the target cell.

28. The method of claim 27, wherein the macroprojectile stopping means is a filter.

29. The method of claim 28, wherein the filter has a pore size of between about 1 and about 8 µm.

30. The method of claim 20, wherein the propelling is by a gas means.

31. The method of claim 30, wherein the gas means is a particle gun.

32. The method of claim 20, wherein the particles are metal particles.

33. The method of claim 32, wherein the metal particles are selected from the group consisting of ferrite crystals, gold and tungsten.

34. The method of claim 20, wherein the population or cells is part of a tissue.

35. The method of claim 34, wherein the tissue is selected from the group consisting of tumor tissue, epidermal tissue, muscle tissue, bone marrow tissue, neural tissue, brain tissue, organ tissue, and human biopsy tissue.

36. The method of claim 34, wherein the coated particles are propelled 50–100 µm into the tissue to contact the membranes of the cells.

37. The method of claim 36, wherein the coated particles are propelled about 50–70 µm into the tissue.

38. The method of claim 20 wherein the labeled cells are living or fixed cells.

39. A method of imaging cells, of claim 38, wherein the cells are labeled by the method wherein the labeled cells are living cells and said cells are imaged within about one minute of the coated particles being propelled at the cell.

40. A method of imaging cells, of claim 38, wherein the cells are labeled by the method wherein the labeled cells are fixed cells and said cells are imaged within lees than about five minutes of the coated particles being propelled at the cells.

41. A method of imaging cells, wherein the cells are labeled by the method of claim 38, wherein the labeled cells are fixed cells and said cells are imaged within less than about thirty minutes of the coated particles being propelled at the cells.

42. The method of claim 20, wherein the cell is a neuron.

43. The method of claim 42, wherein the particle contacts an axon.

44. The method of claim 42, wherein the particle does not contact the cell body.

45. A method for individually labeling cells within a population of cells whereby the cells are differentially labeled relative to neighboring cells within the population, the method comprising propelling a plurality of particles containing a plurality of nucleotide sequences encoding fluorescent proteins having different emission spectra at the population of cells to cause the particles to enter the cells, and allowing expression of the proteins encoded by the nucleotide sequences to occur and thereby differentially label the cells relative to neighboring cells within the population.

46. The method of claim 45, wherein the fluorescent proteins with different emission spectra are red fluorescent protein, green fluorescent protein or variants of green fluorescent protein.

47. The method of claim 45, wherein the propelling is by a gas means.

48. The method of claim 47, wherein the gas means is a particle gun.

49. The method of claim 45, wherein the particles are metal particle.

50. The method of claim 49, wherein the metal particles axe selected from the group consisting of ferrite crystals, gold and tungsten.

51. The method of claim 45, wherein the population of cells is part of a tissue.

52. The method of claim 51, wherein the tissue is selected from the group consisting of tumor tissue, epidermal tissue, muscle tissue, bone marrow tissue, neural tissue, brain tissue, organ tissue, and human biopsy tissue.

53. The method of claim 51, wherein the coated particles are propelled 50–100 µm into the tissue to enter the cells.

54. The method of claim 53, wherein the coated particles are propelled about 50–70 µm into the tissue.

* * * * *